United States Patent [19]

Fukazawa

[11] Patent Number: 5,672,886
[45] Date of Patent: Sep. 30, 1997

[54] SURFACE INSPECTION SYSTEM FOR DETECTING VARIOUS SURFACE FAULTS

[75] Inventor: Chiaki Fukazawa, Saitama-ken, Japan

[73] Assignee: Kabushiki Kaisha Toshiba, Kawasaki, Japan

[21] Appl. No.: 510,302

[22] Filed: Aug. 2, 1995

[30] Foreign Application Priority Data

Aug. 12, 1994 [JP] Japan ..................... 6-190360

[51] Int. Cl.⁶ .......................................... G01N 21/86
[52] U.S. Cl. .................. 250/559.46; 382/149; 356/429; 356/238
[58] Field of Search ................ 250/559.45, 559.46; 356/237, 238, 429–431; 382/149, 159

[56] References Cited

U.S. PATENT DOCUMENTS 5,544,256  8/1996  Brecher et al. ..................... 382/149

FOREIGN PATENT DOCUMENTS

| 0 093 422 | 11/1983 | European Pat. Off. . |
| 0 563 897 | 10/1993 | European Pat. Off. . |
| 53-42431 | 11/1978 | Japan . |
| 61-47362 | 10/1986 | Japan . |
| 2 272 516 | 5/1994 | United Kingdom . |

*Primary Examiner*—Stephone Allen
*Attorney, Agent, or Firm*—Oblon, Spivak, McClelland, Maier & Neustadt, P.C.

[57] ABSTRACT

A surface inspection system including, a detection circuit for detecting an image of a surface fault in a runing sheet material, a fault area judgement circuit connected to the detection circuit for receiving the image and for determining a fault area including a cluster fault composed of the same type of fault parts, and a recognition circuit connected to the detection circuit for receiving the image, connected to the fault area judgement circuit for receiving the fault area, and for recognizing a type and a grade of the cluster fault included in the fault area.

12 Claims, 5 Drawing Sheets

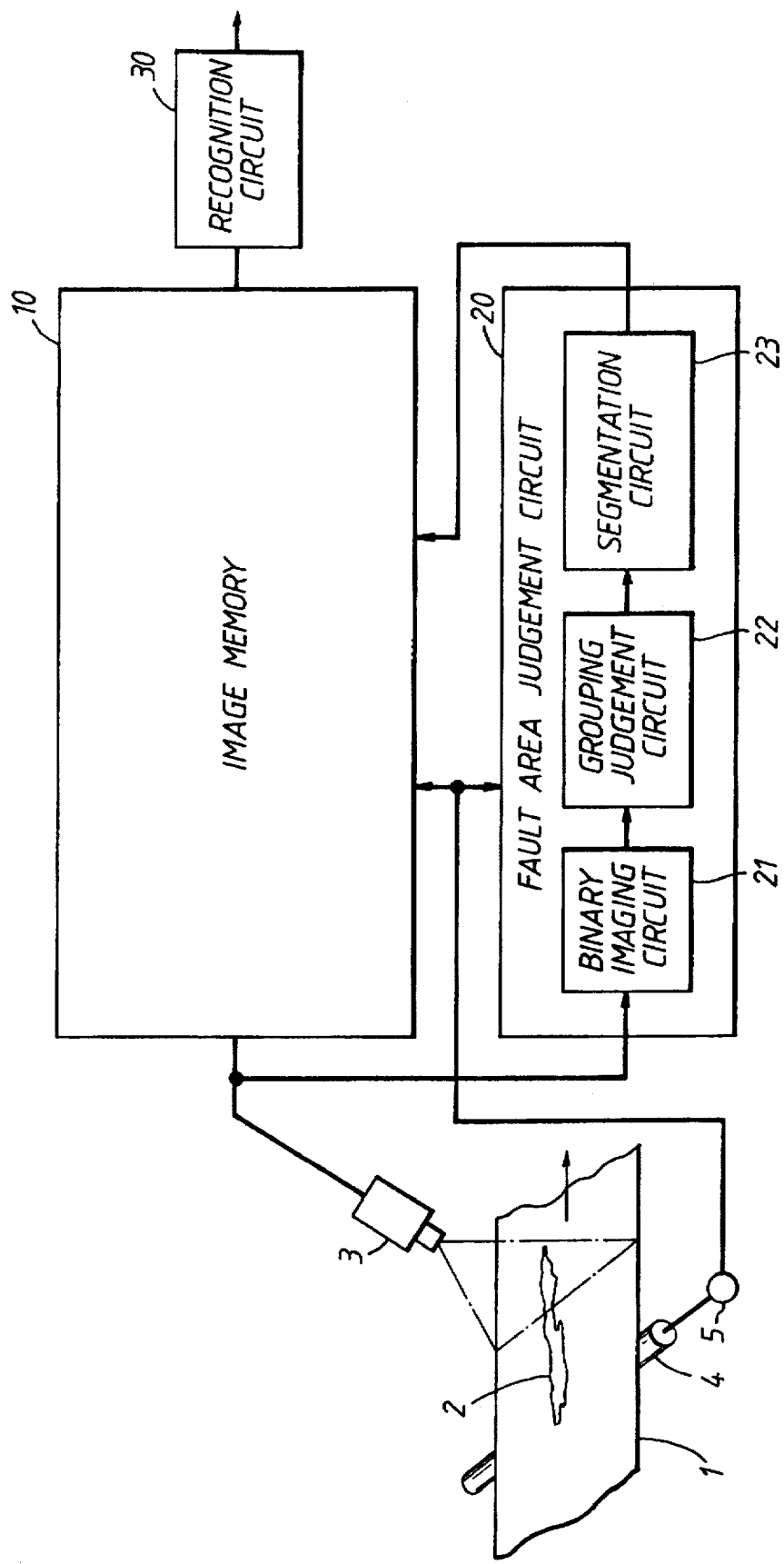

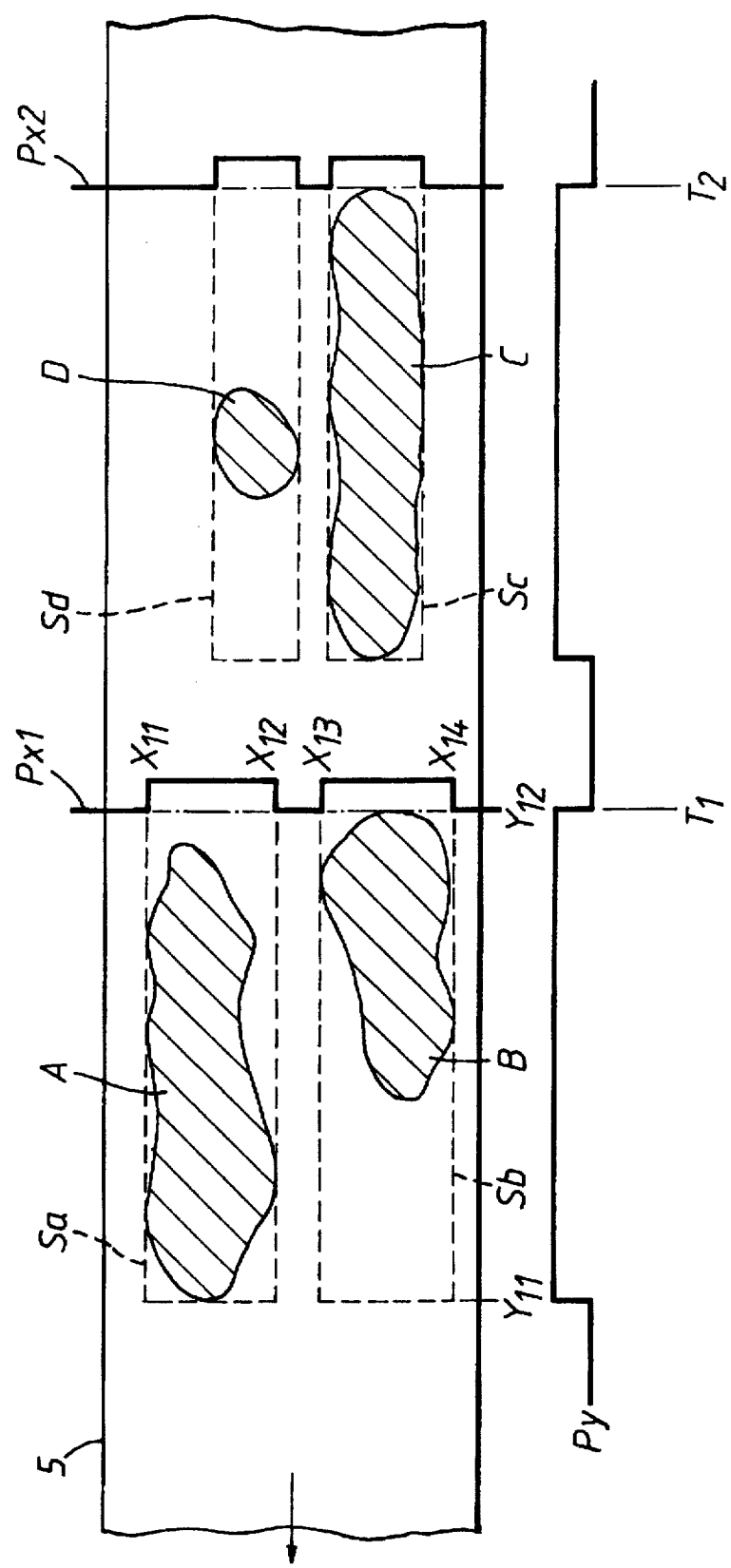

SURFACE INSPECTION SYSTEM FOR DETECTING VARIOUS SURFACE FAULTS

BACKGROUND OF THE INVENTION

1. Field of the Invention

This invention relates to a surface inspection system, and more particularly to a surface inspection system which detects surface faults in a running sheet material.

2. Description of the Related Art

As a prior art surface inspection system, there is, for example, a system such as that shown in FIG. 5. This system is composed of a detector 3 as a detection means which detects an image of a surface fault 2 on a running sheet material 1, a line synchronizing signal generator 5 connected to a roller 4 for detecting the running of sheet material 1, a dividing circuit 6 which divides the surface to be inspected of sheet material 1 into divided surfaces of a specified size in the width direction and length direction without any relation to the position of faults, and a recognition circuit 7 which judges the types and grades of faults contained in each divided surface.

In this way, this surface inspection system is designed automatically to inspect the surface of sheet material 1. FIG. 6 shows an example of faults on the surface of sheet material 1 and an example of the composition of divided surfaces on the surface of sheet material 1. In FIG. 6, A is a group of linear faults distributed in the length direction of sheet material 1, B is a group of dot-shaped faults, C is an intermittent narrow linear fault, and D is an isolated dot-shaped fault. Also, $L_1$, $L_2$, $L_3$, $L_4$ and $L_5$ are dividing lines in the length direction and $D_1$, $D_2$ and $D_3$ are dividing lines in the width direction, and the surface of sheet material 1 is divided into multiple divided surfaces by these dividing lines.

The prior art surface inspection system described above is disclosed in Japanese Patent Publication (Kokoku), No. Sho. 61-47362 published on Oct. 18, 1986.

In the prior art surface inspection system, the surface subject to inspection of the sheet material was divided into divided surfaces of a specified size, and the types and grades of the faults were judged for every fault contained in each of those divided surfaces. However, as shown in the examples in FIG. 6, most of the surface faults of the sheet material should be judged as a single fault composed of a group of several faults. The shapes of the faults are generally complex, and the positions of the faults are indeterminate. As the surface subject to inspection of the sheet material is divided into divided surfaces with a specified size in the width direction and the length direction, it happens that faults such as faults A, B and C, straddle multiple divided surfaces. Thus, there is a problem that it is difficult to correctly judge the types and grades of the these faults.

SUMMARY OF THE INVENTION

Accordingly, one object of this invention is to provide a surface inspection system which can correctly recognize at high speed in real time the type and grade of each fault, even in cases when there are various shapes of surface faults on the sheet material and those surface faults are composed of multiple parts.

These and other objects of this invention can be achieved by providing a surface inspection system including, a detection circuit for detecting an image of a surface fault in a running sheet material, a fault area judgement circuit connected to the detection circuit for receiving the image and for determining a fault area including a cluster fault composed of the same type of fault parts, and a recognition circuit connected to the detection circuit for receiving the image, connected to the fault area judgement circuit for receiving the fault area, and for recognizing a type and a grade of the cluster fault included in the fault area.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a block diagram showing the composition of a surface inspection system according to an embodiment of this invention;

FIG. 3 is a diagram to illustrate the fault area determination operation of excision circuit 23 by the projection method;

DETAILED DESCRIPTION OF THE PREFERRED EMBODIMENTS

Figure 2A:
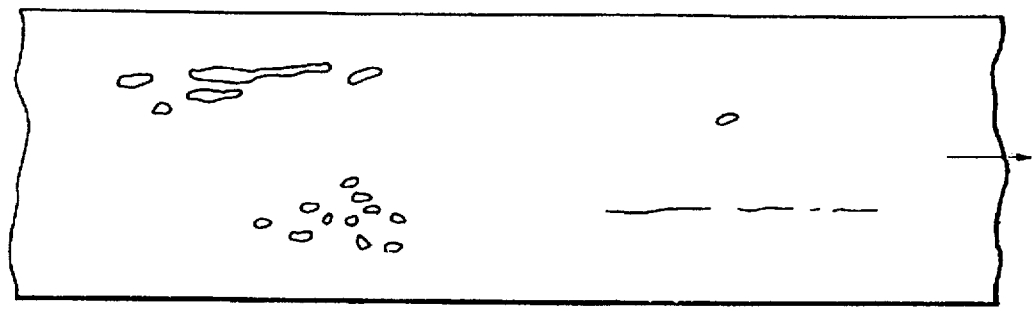
FIGS. 2a–2c are diagrams to illustrate the fault area determination processing method by fault area judgement circuit 20 in FIG. 1.

Referring now to the drawings, wherein like reference numerals designate identical or corresponding parts throughout the several views, the embodiments of this invention will be described below.

FIG. 1 is a block diagram showing the composition of a surface inspection system according to an embodiment of this invention. In FIG. 1, 10 is an image memory which stores images of specified areas of sheet material 1 detected by detector 3. A fault area judgement circuit 20 as the fault area judgement means is provided with a binary imaging circuit 21 which makes binary images from the output images of detector 3, a grouping judgement circuit 22 which judges faults composed of multiple parts as clusters from these binary image patterns, and a segmentation circuit 23 which determines the fault areas by judging the separations of fault areas judged as clusters. 30 is a recognition circuit as the recognition means which recognizes the types and grades of the faults contained in the determined fault areas almost the same as prior art recognition circuit 7 does. The design is that, when a fault area is determined by fault area judgement circuit 20, an image of the specified area is outputted to recognition circuit 30 from image memory 10. Image memory 10 also stores a fresh detected image from detector 3.

Figure 2B:
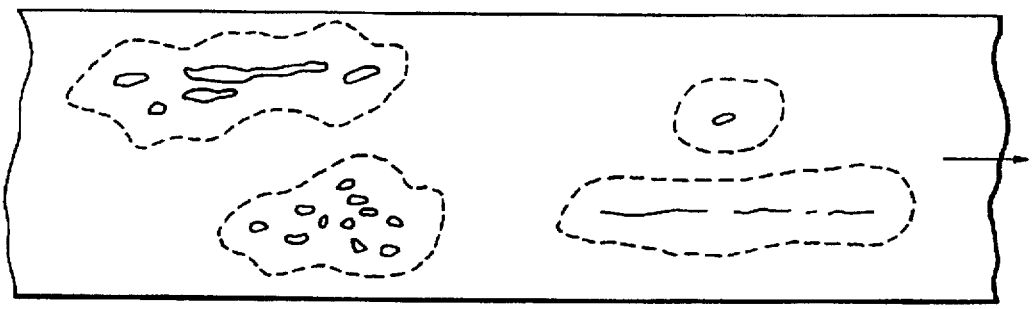
Figure 2C:
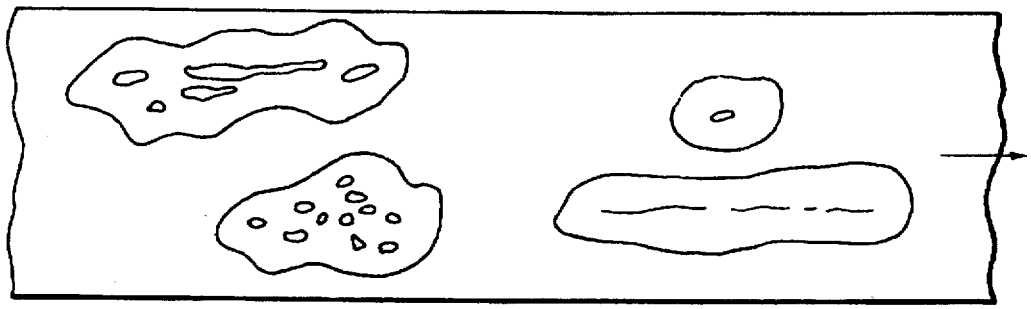

Next, the fault area determination operation by fault area judgement circuit 20 is described using FIG. 2. Binary imaging circuit 21 obtains a binary image by discriminating the input image at an appropriate judgement level (FIG. 2(a)). Grouping judgement circuit 22 judges the "clustering" of the parts which compose each fault by executing an expansion processing or an enlargement processing on that binary image pattern. Specifically, it links a fault to a neighbouring fault by expanding (enlarging) that fault up to a specified area around the fault point. By this means, faults A, B, C and D in FIG. 2(b) become cluster faults composed of the areas surrounded by the dotted lines. Segmentation circuit 23 determines each fault area by judging the separation of the cluster faults judged by grouping judgement circuit 22. It performs, for instance, a labelling process as that determination process. This is, the judging of the connectivity of each pixel which composes the fault and assigning a label to each fault area. This discrimination method is comparatively lengthy because the processing is complex. As opposed to this, as an alternative processing method, it is possible to adopt the projection method which determines the fault areas from projections in the running direction and the width direction of sheet material 1. This method is comparatively simple and speedy.

Figure 4:
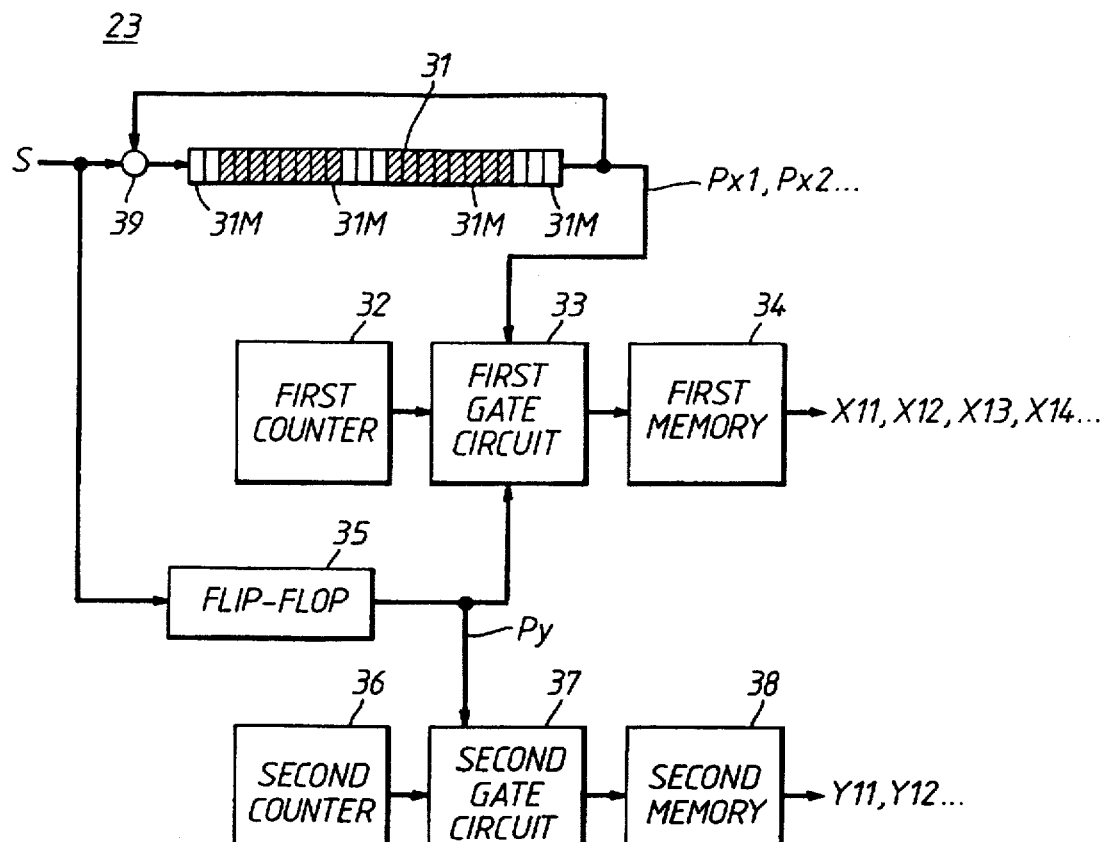
FIG. 4 is a circuit diagram of one example of excision circuit 23.
Figure 5:
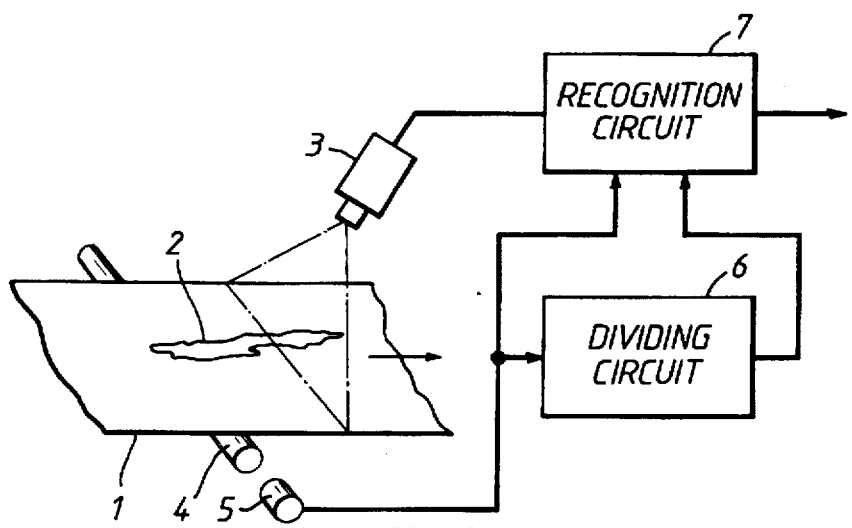
FIG. 5 is a block diagram of a prior art surface inspection system.
Figure 6:
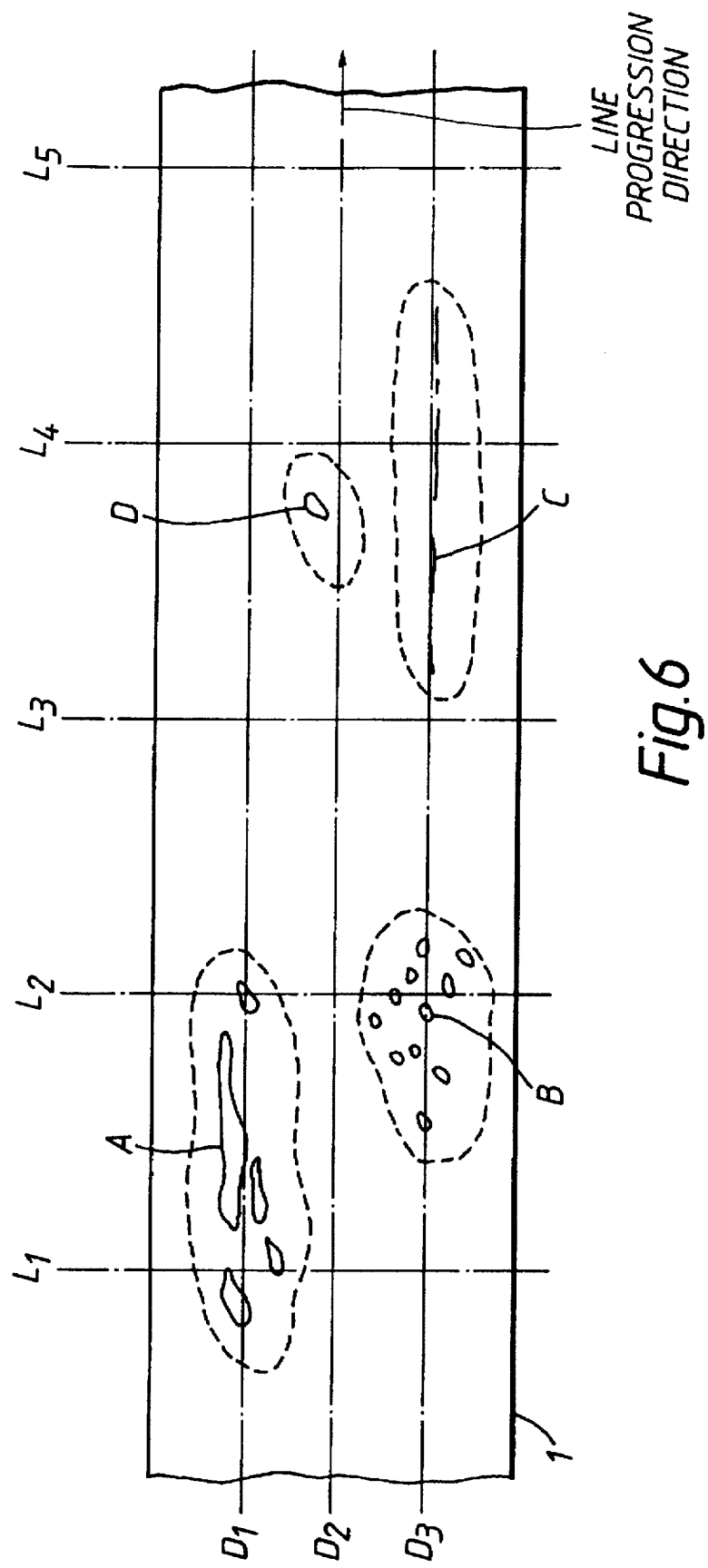
FIG. 6 is a diagram to illustrate the operation of the prior art shown in FIG. 5.

This projection method is described below. In FIG. 3, A, B, C and D are cluster faults judged by grouping judgement circuit 22. FIG. 4 is a circuit diagram of one example of segmentation circuit 23. In FIG. 4, a shift register 31 is provided with a plurality of memories 31M of the number corresponding to the number of the pixels of running sheet material 1 in the width direction. Shift register 31 receives an output S of grouping judgement circuit 22 through a logic OR circuit 39 and stores "1" (fault signal) in memories 31M corresponding to pixels included in the cluster fault. The output of shift register 31 is fed back to an input of logic OR circuit 39. Logical sum (OR) of output S of grouping judgement circuit 22 and the output of shift register 31 is inputted to shift register 31. Thus, shift register 31 accumulates "1" (fault signal) in memories 31M for each scanning. Shift register 31 repeats this memory operation every time of scanning thereby to obtain a projection Px of the cluster fault in the width direction. A flip-flop 35 also receives output S of grouping judgement circuit 22, and stores "1" when the scanning is executed on the cluster fault. Thus, flip-flop 35 outputs a projection Py of the cluster fault in the running direction of sheet material 1.

A first counter 32 counts the number of pixels in the width direction from the end portion of running sheet material 1 as a starting point, when the scanning is started. Next, at a cut-line (falling point) of projection Py in the running direction, for example at a time T1, projection Px1 in the width direction is read out. The values of first counter 32 at the rising and falling points of projection Px1, such as values X11, X12, X13 and X14 are stored in a first memory 34 through a first gate circuit 33.

A second counter 36 counts the number of pixels in the running direction from the tip portion of running sheet material 1 as a starting point. At rising and falling points of projection Py in the running direction, the values of projection Py, for example Y11 and Y12, are stored in a second memory 38 through a second gate circuit 37.

Thus, the fault area for the cluster fault is determined. As cluster fault A, for example, it is located in a fault area Sa between addresses X11 and X12 in the width direction and between addresses Y11 and Y12 in the running direction. Cluster fault B is located in a fault area Sb between addresses X13 and X14 in the width direction and between addresses Y11 and Y12 in the running direction.

Based on projection Px2 at a time T2, which is a next cut-line of projection Py and rising and falling points of projection Py in the running direction, fault areas Sc and Sb are determined for cluster faults C and D, respectively.

As described above, fault areas Sa, Sb, Sc and Sd which respectively surround cluster faults A, B, C and D can be obtained from these running direction and width direction projections Py and Px in segmentation circuit 23.

When using this embodiment as stated above, even if a single fault is divided into several parts and, moreover, each part has a complex shape, the judgement of a cluster fault by the expansion processing or the like, and the separation of cluster faults by projection method, are executed. By this means, the fault area is determined by a simple process and almost as speedily as in real time. Furthermore, the types and grades of the fault contained in that fault area can be recognized.

As described above, the surface inspection system according to this invention is provided with a detection device which detects an image of a surface fault in a running sheet material, a fault area judgement device which determines a fault area including a cluster fault composed of the same type of fault points by judging the fault distribution state from the surface fault images which have been detected, and a recognition device which recognizes the type and grade of the cluster fault contained in the fault area which have been determined.

Therefore, in a case when there are surface faults with various configurations on the sheet material and those surface faults are composed of multiple fault parts, the types and grades of the faults can be correctly and speedily recognized.

Obviously, numerous modifications and variations of the present invention are possible in light of the above teachings. It is therefore to be understood that within the scope of the appended claims, the invention may be practiced otherwise than as specifically described herein.

What is claimed is:

1. A surface inspection system, comprising:

detection means for detecting an image of a surface fault in a running sheet material;

fault area judgement means connected to said detection means for receiving said image and for determining a fault area including a cluster fault composed of the same type of fault parts; and recognition means connected to said detection means for receiving said image, connected to said fault area judgement means for receiving said fault area, and for recognizing a type and a grade of said cluster fault included in said fault area.

2. A surface inspection system, comprising:

detection means for detecting an image of a surface fault in a running sheet material;

fault area judgement means connected to said detection means for receiving said image and for determining a fault area including a cluster fault composed of the same type of fault parts; and recognition means connected to said detection means for receiving said image, connected to said fault area judgement means for receiving said fault area, and for recognizing a type and a grade of said cluster fault included in said fault area;

wherein said fault are judgement means includes:

a binary imaging circuit connected to said detection means for receiving said image and for binary imaging said image to generate binary image patterns;

a grouping judgement circuit connected to said binary imaging circuit for receiving said binary image patterns and for judging a fault composed of the same type of said fault parts as said cluster fault from said binary image patterns; and a segmentation circuit connected to said grouping judgement circuit for receiving said cluster fault and for determining said fault area including said cluster fault by judging the separation of said cluster fault.

3. The surface inspection system according to claim 2, wherein:

said grouping judgement circuit judges a specified area around pixels of said fault parts in said binary image patterns as said cluster fault by one of an expansion processing and an enlargement processing.

4. The surface inspection system according to claim 2, wherein:

said segmentation circuit determines said fault area including said cluster fault by judging the connectivity of each of pixels of said cluster fault and numbering said pixels.

5. The surface inspection system according to claim 2 wherein:

said segmentation circuit takes projections of said cluster fault in the length direction and the width direction of said running sheet material and determines said fault area including said cluster fault from said projections.

6. The surface inspection system according to claim 5, wherein:

said segmentation circuit takes said projections of said cluster fault in the width direction as a width projection at each end of length projection of said cluster fault in the length direction, and determines a rectangular area determined by said width projection and said length projection as said fault area including said cluster fault.

7. A surface inspection system, comprising:

a detector detecting an image of a surface fault in a running sheet material;

a fault area judgement circuit connected to said detector and receiving said image and for determining a fault area including a cluster fault composed of the same type of fault parts; and a recognition circuit connected to said detector and receiving said image, connected to said fault area judgement circuit and receiving said fault area, and for recognizing a type and a grade of said cluster fault included in said fault area.

8. A surface inspection system, comprising:

a detector detecting an image of a surface fault in a running sheet material;

a fault area judgement circuit connected to said detector and receiving said image and for determining a fault area including a cluster fault composed of the same type of fault parts; and a recognition circuit connected to said detector and receiving said image, connected to said fault area judgement circuit and receiving said fault area, and for recognizing a type and a grade of said cluster fault included in said fault area;

wherein said fault are judgement circuit includes:

a binary imaging circuit connected to said detection means for receiving said image and for binary imaging said image to generate binary image patterns;

a grouping judgement circuit connected to said binary imaging circuit for receiving said binary image patterns and for judging a fault composed of the same type of said fault parts as said cluster fault from said binary image patterns; and a segmentation circuit connected to said grouping judgement circuit for receiving said cluster fault and for determining said fault area including said cluster fault by judging the separation of said cluster fault.

9. The surface inspection system according to claim 8, wherein:

said grouping judgement circuit judges a specified area around pixels of said fault parts in said binary image patterns as said cluster fault by one of an expansion processing and an enlargement processing.

10. The surface inspection system according to claim 8, wherein:

said segmentation circuit determines said fault area including said cluster fault by judging the connectivity of each of pixels of said cluster fault and numbering said pixels.

11. The surface inspection system according to claim 8, wherein:

said segmentation circuit takes projections of said cluster fault in the length direction and the width direction of said running sheet material and determines said fault area including said cluster fault from said projections.

12. The surface inspection system according to claim 11, wherein:

said segmentation circuit takes said projections of said cluster fault in the width direction as-a width projection at each end of length projection of said cluster fault in the length direction, and determines a rectangular area determined by said width projection and said length projection as said fault area including said cluster fault.

* * * * *